(12) United States Patent
Bessant (10) Patent No.: US 11,945,644 B2
(45) Date of Patent: Apr. 2, 2024

(54) AEROSOL-GENERATING SYSTEM

(71) Applicant: Altria Client Services LLC, Richmond, VA (US)

(72) Inventor: Michel Bessant, Carouge (CH)

(73) Assignee: Altria Client Services LLC, Richmond, VA (US)

( * ) Notice: Subject to any disclaimer, the term of this patent is extended or adjusted under 35 U.S.C. 154(b) by 54 days.

(21) Appl. No.: 17/315,792

(22) Filed: May 10, 2021

(65) Prior Publication Data

US 2021/0309445 A1 Oct. 7, 2021

Related U.S. Application Data

(63) Continuation of application No. 16/257,892, filed on Jan. 25, 2019, now Pat. No. 11,091,314, which is a
(Continued)

(30) Foreign Application Priority Data

Sep. 12, 2016 (EP) .................................... 16188321

(51) Int. Cl.
*B65D 83/68* (2006.01)
*A61M 11/04* (2006.01)
(Continued)

(52) U.S. Cl.
CPC ......... *B65D 83/685* (2013.01); *A61M 11/042* (2014.02); *A61M 15/00* (2013.01);
(Continued)

(58) Field of Classification Search
CPC .. B65D 83/685; B65D 83/384; B65D 83/752; A61M 11/042; A61M 15/00;
(Continued)

(56) References Cited

U.S. PATENT DOCUMENTS 4,470,697 A 9/1984 Chraplyvy et al.
5,721,430 A * 2/1998 Wong ................. G01N 21/3518
250/338.5
(Continued)

FOREIGN PATENT DOCUMENTS

AU 2009267544 A1 1/2010
CN 203646504 U 6/2014
(Continued)

OTHER PUBLICATIONS

Office Action for corresponding Chinese Application No. 201780050595.3 dated Apr. 25, 2021.
(Continued)

*Primary Examiner* — Marcus H Taningco
(74) *Attorney, Agent, or Firm* — Harness, Dickey & Pierce, P.L.C.

(57) ABSTRACT

A handheld aerosol-generating device may include an emitter configured to emit light, a sensor configured to receive light, and an aerosol chamber configured to hold an aerosol. The emitter may emit light into the aerosol chamber. The sensor may receive light from the aerosol chamber and measure at least one wavelength of the spectrum of the received light. Direct measurement of parameters, and/or the presence, of the aerosol in the aerosol chamber may be enabled, where the direct measurement of parameters of the aerosol in the aerosol chamber may enable optimal operation of an aerosol-generating system that may be the handheld aerosol-generating device.

18 Claims, 9 Drawing Sheets

Related U.S. Application Data continuation of application No. 15/700,309, filed on Sep. 11, 2017, now Pat. No. 10,189,632, which is a continuation of application No. PCT/EP2017/069565, filed on Aug. 2, 2017.

(51) Int. Cl.

| | | |
|---|---|---|
| *A61M 15/00* | (2006.01) | |
| *A61M 15/06* | (2006.01) | |
| *B65D 83/14* | (2006.01) | |
| *B65D 83/38* | (2006.01) | |
| *G01N 21/31* | (2006.01) | |
| *H05B 1/02* | (2006.01) | |
| *G01N 15/00* | (2006.01) | |

(52) U.S. Cl.
CPC ........... *A61M 15/06* (2013.01); *B65D 83/384* (2013.01); *B65D 83/752* (2013.01); *G01N 21/31* (2013.01); *H05B 1/0244* (2013.01); *A61M 2205/3313* (2013.01); *A61M 2205/8206* (2013.01); *G01N 2015/0026* (2013.01); *G01N 2015/03* (2013.01); *G01N 21/314* (2013.01); *H05B 1/0247* (2013.01); *H05B 2203/021* (2013.01)

(58) Field of Classification Search
CPC .......... A61M 15/06; A61M 2205/3313; A61M 2205/8206; G01N 21/31; G01N 21/314; G01N 2015/0026; G01N 2015/03; H05B 1/0244; H05B 1/0247; H05B 2203/02
See application file for complete search history.

(56) References Cited

U.S. PATENT DOCUMENTS

| | | | |
|---|---|---|---|
| 7,046,347 | B1 | 5/2006 | Amend et al. |
| 2003/0223063 | A1 | 12/2003 | Hill et al. |
| 2010/0236545 | A1 | 9/2010 | Kern |
| 2012/0080611 | A1 | 4/2012 | Jones et al. |
| 2013/0008436 | A1* | 1/2013 | Von Hollen ........ A61M 15/009 128/200.14 |
| 2015/0073334 | A1 | 3/2015 | Hetzel et al. |
| 2015/0237915 | A1 | 8/2015 | Liu |
| 2015/0351456 | A1 | 12/2015 | Johnson et al. |
| 2016/0219938 | A1 | 8/2016 | Mamoun et al. |
| 2016/0286862 | A1 | 10/2016 | Silvetrini |
| 2016/0302488 | A1* | 10/2016 | Fernando ................ A24F 40/51 |
| 2017/0265524 | A1 | 9/2017 | Cadieux et al. |
| 2017/0333645 | A1 | 11/2017 | Alizoti et al. |
| 2017/0347710 | A1* | 12/2017 | Hon .................... A61M 11/042 |
| 2018/0007968 | A1 | 1/2018 | Sur |
| 2018/0007970 | A1 | 1/2018 | Sur |
| 2018/0161531 | A1 | 6/2018 | Costella et al. |

FOREIGN PATENT DOCUMENTS

| | | |
|---|---|---|
| CN | 203986094 U | 12/2014 |
| CN | 204540813 U | 8/2015 |
| CN | 204949505 U | 1/2016 |
| CN | 205456039 U | 8/2016 |
| EP | 2493342 A1 | 9/2012 |
| GB | 2524779 A | 10/2015 |
| JP | 2010-271213 A | 12/2010 |
| RU | 121706 U1 | 11/2012 |
| WO | WO-97/25609 A1 | 7/1997 |
| WO | WO-2004047570 A2 | 6/2004 |
| WO | WO-2007098392 A2 | 8/2007 |
| WO | WO-2008133091 A1 | 11/2008 |
| WO | WO-2009095679 A2 | 8/2009 |
| WO | WO-2011050964 A1 | 5/2011 |
| WO | WO-2015082560 A1 | 6/2015 |
| WO | WO-2015/124688 A1 | 8/2015 |
| WO | WO-2016/079533 A1 | 5/2016 |
| WO | WO-2016/101203 A1 | 6/2016 |
| WO | WO-2017199215 A1 | 11/2017 |

OTHER PUBLICATIONS

Decision of Grant for corresponding Japanese Application No. 2019-513025 dated Nov. 8, 2021.
Office Action for corresponding Japanese Application No. 2019-513025 dated Jun. 21, 2021.
Office Action for corresponding Chinese Application No. 201780050595.3 dated Nov. 10, 2021.
Office Action for corresponding European Application No. 17746132.4 dated Aug. 4, 2021.
Notice of Allowance for corresponding Chinese Application No. 201780050595.3 dated Feb. 11, 2022.
Office Action for Korean Application No. 10-2019-7004829 date Sep. 1, 2022 and English translation.
Notice of Allowance for Korean Application No. 10-2019-7004829 dated Nov. 3, 2022 and English translation.
European Search Report for European Patent Application No. 16188321.0 dated May 12, 2017.
Wikipedia—"Infrared Spectroscopy".
International Search Report and Written Opinion for corresponding PCT Application No. PCT/EP2017/069565 dated Oct. 20, 2017.
E. Deconinck et al., "Discriminating nicotine and non-nicotine containing e-liquids using infrared spectroscopy", "Journal of Pharmaceutical and Biomedical Analysis", 2015, pp. 333-347.
T.A. Vincent et al., "A Low cost MEMS based NDIR system for the monitoring of carbon dioxide in breath analysis at ppm levels", "Sensors and Actuators B: Chemical, 2016", pp. 954-964.
M. Segal-Rosenheimer, "Extraction of optical constants from mid-IR spectra of small aerosol particles" "Journal of Quantitative Spectroscopy & Radiative Transfer", 2009, pp. 415-426.
Written Opinion for corresponding Application No. PCT/EP2017/069565 dated Aug. 17, 2018.
International Preliminary Report on Patentability dated Nov. 19, 2018 in corresponding Application No. PCT/EP2017/069565.
Office Action for corresponding Gulf Co-operation Application No. GC 2017-33936 dated Mar. 27, 2019.
Russian Decision to Grant dated Oct. 2, 2020, issued in corresponding RU Application No. 2019110843.
Office Action for Argentine Application No. 20170102513 dated Sep. 15, 2020.
C. Calaza et al, "A MEMS-based thermal infrared emitter for an integrated NDIR spectrometer" Microsyst Technol (2012) 18:1147-1154., Mar. 4, 2012.
Office Action for corresponding European Application No. 17746132.4 dated Feb. 24, 2023.

\* cited by examiner

AEROSOL-GENERATING SYSTEM

CROSS-REFERENCE TO RELATED APPLICATIONS

This application is a continuation of U.S. application Ser. No. 16/257,892, filed Jan. 25, 2019, which is a continuation of U.S. application Ser. No. 15/700,309, filed Sep. 11, 2017, which is a continuation of International Application No. PCT/EP2017/069565, filed on Aug. 2, 2017, which claims priority under 35 U.S.C. § 119 to European Application No. 16188321.0, filed on Sep. 12, 2016, the entire contents of each of which are incorporated herein by reference.

BACKGROUND

Field

Example embodiments relate to aerosol-generating systems comprising an emitter of electromagnetic radiation and a receiver for receiving electromagnetic radiation, and an aerosol chamber holding ("containing," "including," etc.) an aerosol to be analyzed.

Description of Related Art

Handheld electrically operated aerosol-generating systems may include a device portion comprising a battery and control electronics and a separate cartridge comprising a supply of liquid aerosol-forming substrate held in a liquid storage portion and an electrically operated vaporizer or heater element. The quality of the generated aerosol may differ from device to device. Also, the quality of the generated aerosol may depend upon the liquid aerosol-forming substrate included in the aerosol-generating systems, since different liquid aerosol-forming substrates with, for example, different flavor constituents can be used. Furthermore, the performance of an aerosol-generating system may change over time. The quality of the aerosol generated by an aerosol-generating system may also depend upon an intensity of a draw of the generated aerosol out of the aerosol-generating system, a duration of a draw of the generated aerosol out of the aerosol-generating system, if it is the first, second, etc. draw, or if the aerosol-generating system is clean or dirty. In some aerosol-generating systems, such as disclosed in EP 2 493 342, the only feedback the system obtains is the impedance of the heater element. However, the quality of the generated aerosol is not directly measured. Also, the amount of liquid aerosol-forming substrate left in the liquid storage portion is not directly measured.

It is desirable to provide an aerosol-generating system which directly measures the quality of the generated aerosol. Also, it is desirable to provide an aerosol-generating system which directly measures the amount of liquid aerosol-forming substrate held in a liquid storage portion.

SUMMARY

According to some example embodiments, a handheld aerosol-generating device may include an aerosol chamber configured to hold an aerosol, an emitter configured to emit light into the aerosol chamber, and a sensor configured to receive light from the aerosol chamber and measure at least one wavelength of a spectrum of the received light.

The emitter may be configured to emit light having wavelengths between 200 nanometers and 30 micrometers, and the sensor may be configured to receive light having wavelengths between 200 nanometers and 30 micrometers.

The handheld aerosol-generating device may include at least two emitters and at least two sensors, the at least two emitters including a first emitter configured to emit light having a first wavelength and a second emitter configured to emit light having a second wavelength, the first wavelength different from the second wavelength.

The first emitter may be configured to emit light having a wavelength of about 3.0 micrometers.

The second emitter may be configured to emit light having a wavelength of about 6.3 micrometers.

At least one of the emitter and the sensor may be configured to be isolated from the aerosol in the aerosol chamber.

The at least two sensors may include a first sensor that is configured to receive light having the first wavelength and a second sensor configured to receive light having the second wavelength.

The aerosol chamber may include an at least partially transparent housing.

At least one of the emitter and the sensor may be one of a microelectromechanical system, an opto-semiconductor, a compound semiconductor, and a hybrid electronic device.

The handheld aerosol-generating device may include more than two emitters; and more than two sensors. The more than two emitters may be arranged in a semicircular matrix of emitters, and the more than two sensors may be arranged in a semicircular matrix of sensors. Each row of the semicircular matrix of emitters may include a plurality of emitters, and different rows of emitters of the semicircular matrix of emitters may be configured to emit light having different wavelengths. Each row of the semicircular matrix of sensors may include sensors configured to receive light of a wavelength corresponding to the wavelength emitted by a corresponding row of emitters of the semicircular matrix of emitters.

The emitter may be configured to emit light having a wavelength between 2.8 micrometers and 3.2 micrometers.

The emitter may be configured to emit light having a wavelength between 6.0 micrometers and 6.6 micrometers.

The emitter may be a multiple narrow-band emitter. The sensor may be a multiple narrow-band sensor.

The sensor may be configured to detect at least one of $CO_2$, Water, benzene, 1,3-butadiene, formaldehyde, nicotine and carboxylic acid.

According to some example embodiments, a method for manufacturing a handheld aerosol-generating device may include providing a housing enclosing a power supply and electric circuitry configured to control the power supply, providing an emitter configured to emit light, the emitter connected to the electric circuitry, providing a sensor configured to receive light, the sensor connected to the electric circuitry, and providing an aerosol chamber configured to hold an aerosol. The emitter may be further configured to emit light into the aerosol chamber, and the sensor may be further configured to receive light from the aerosol chamber and measure at least one wavelength of a spectrum of the received light.

The emitter may be configured to emit light having wavelengths between 200 nanometers and 30 micrometers, and the sensor may be configured to receive light having wavelengths between 200 nanometers and 30 micrometers.

The emitter may include at least two emitters and at least two sensors. The at least two emitters may include a first emitter configured to emit light having a first wavelength and a second emitter configured to emit light having a second wavelength, the first wavelength different from the second wavelength.

At least one of the emitter and the sensor may be configured to be isolated from the aerosol in the aerosol chamber.

BRIEF DESCRIPTION OF THE DRAWINGS

Example embodiments will now be described, by way of example only, with reference to the accompanying drawings, in which.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

When the terms "about" or "substantially" are used in this specification in connection with a numerical value, it is intended that the associated numerical value include a tolerance of ±10% around the stated numerical value. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure.

According to some example embodiments there is provided an aerosol-generating system comprising an emitter. The emitter is configured to emit light. The aerosol-generating system further comprises a sensor, which is configured to receive light. Also, the aerosol-generating system comprises an aerosol chamber, configured to comprise ("include," "hold," "contain," etc.) an aerosol. The emitter is configured to emit light into the aerosol chamber. The sensor is configured to receive light from the aerosol chamber and measure at least one wavelength of the spectrum of the received light.

The aerosol generating system may comprise a handheld aerosol-generating device. The handheld aerosol-generating device may be configured to generate an aerosol for an adult vaper. The handheld aerosol-generating device may comprise a mouthpiece ("outlet end") through which aerosol generated by the device may be drawn out of the device. The aerosol-generating system may be a battery operated device. The aerosol-generating system may comprise a housing holding a battery and the emitter and the sensor. The device may be a portable device that is comfortable to hold between the fingers of a single hand. The device may be substantially cylindrical in shape and have a length of between 70 mm and 200 mm. The maximum diameter of the device may be between 10 mm and 30 mm.

The inventive aerosol-generating system may enable direct measurement of parameters, and/or the presence, of the aerosol in the aerosol chamber. This direct measurement of parameters of the aerosol in the aerosol chamber may enable optimal operation of the aerosol-generating system. The aerosol chamber may be a passage or path within the aerosol-generating system, through which aerosol-forming substrate in vaporized form flows. The aerosol chamber may also be a generating chamber, in which the liquid aerosol-forming substrate is vaporized and an aerosol is formed. Generally, the aerosol chamber may be an open or closed chamber in which vaporized aerosol-forming substrate or an aerosol is present.

The aerosol in the aerosol chamber may be a vaporized aerosol-forming substrate. The vaporized aerosol-forming substrate may comprise multiple vapor components. The vaporized aerosol-forming substrate is provided to form an aerosol. During vaporization of a liquid aerosol-forming substrate, unwanted products may form. The formation of unwanted products should be prevented by the heating regime which results in the vaporized aerosol-forming substrate. However, as outlined above, the vaporization of a liquid aerosol-forming substrate depends on multiple factors such as the type of the liquid aerosol-forming substrate, the number ("quantity") of heating processes, etc. The aerosol-generating system according to some example embodiments now provides a possibility to measure the type and the amount of at least one of the elements of the vaporized aerosol-forming substrate directly.

The measurement may comprise the determination of at least one component ("element") of the vaporized aerosol-forming substrate. In this regard, the spectrum of the vaporized aerosol-forming substrate is analyzed. The spectrum or electromagnetic spectrum of the vaporized aerosol-forming substrate characterizes the elements of the vaporized aerosol-forming substrate by a characteristic distribution of electromagnetic radiation absorbed by the vaporized aerosol-forming substrate.

In more detail, every element of the vaporized aerosol-forming substrate is able to absorb electromagnetic waves with certain frequencies or wavelengths. In some example embodiments, Infrared- or IR-spectroscopy may be used. If light is directed on these elements, they will absorb certain wavelengths of the light. Thus, every element of the vaporized aerosol-forming substrate has ("is associated with") a characteristic spectroscopic distribution or spectrum which can be observed. In the observed spectrum, certain peaks can be observed which correspond to absorbed light with certain frequencies. Typically, every element absorbs light with different wavelength, thus every element shows multiple absorption peaks in the spectrum. The wavelength and the amplitude of these absorption peaks are indicative of the component. Thus, the reliability of the measurement may be enhanced by measuring multiple absorption peaks and/or the amplitude of the peaks. The observation may include the utilization of an emitter, configured to emit electromagnetic waves and a sensor, configured to receive electromagnetic waves. In the following, the general term "electromagnetic waves" is denoted by the more specific term "light". It should, however, be noted that no wavelengths are excluded by the term "light". The emitter may be configured to emit light with wavelengths between 200 nanometers and 30 micrometers and the receiver may be configured to receive light with wavelengths between 200 nanometers and 30 micrometers. Within this wavelength spectrum, unwanted products may be determined in aerosol-forming substrate such as e-liquid for e-cigarettes ("e-vaping devices").

The emitter emits light in the direction of the aerosol, for example the vaporized aerosol-forming substrate, and the vaporized aerosol-forming substrate absorbs certain wavelengths of the light according to the elements present in the vaporized aerosol-forming substrate. In other words, depending upon the elements present in the vaporized aerosol-forming substrate, certain wavelengths of the light, which is emitted by the emitter, is at least partially absorbed by the vaporized aerosol-forming substrate, while other wavelengths may pass through the vaporized aerosol-forming substrate. Thus, a characteristic distribution of electromagnetic radiation passes through the vaporized aerosol-forming substrate, characterizing the specific composition of the vaporized aerosol-forming substrate. This characteristic distribution contains the information about the specific elements of the vaporized aerosol-forming substrate as well as the amount of these elements in the vaporized aerosol-forming substrate.

The sensor is configured to receive this characteristic distribution, which passes through the vaporized aerosol-forming substrate. In this regard, the sensor may be configured to receive only a single wavelength of this spectrum. In this case, the sensor is provided to detect a single absorption band and thus a single element within the vaporized aerosol-forming substrate. In more detail, a specific component, which is to be detected by the sensor, may absorb a specific wavelength. The emitter may be configured to emit light with this wavelength and the sensor may be configured to receive light with this wavelength. When the sensor receives light with this specific wavelength, the sensor detects that the element is not present in the aerosol chamber. If the sensor receives no light or light with an intensity which is below a particular (or alternatively, predetermined) threshold, the sensor detects that the element is present in the aerosol chamber. This can be utilized to detect an unwanted product in the vaporized aerosol-forming substrate. Thus, the sensor detects that a specific unwanted product is present in the vaporized aerosol-forming substrate if the sensor does not detect the wavelength, which is emitted by the emitter or detects only a low amount of the light, which is emitted by the emitter.

The emitter may be configured to emit light with multiple wavelengths and the sensor may be configured to receive this light. The emitter/sensor may be configured as a wide bandgap emitter/sensor such as a wide bandgap microelectromechanical system emitter/sensor. Thus, the electromagnetic spectrum of the aerosol-generating substrate can be observed with the wide bandgap emitter and sensor. In this way, the presence of different elements within the vaporized aerosol-forming substrate can be determined at the same time. Also, the reliability of the detection of a single element may be enhanced, since multiple absorption bands related to a single element may be detected.

Also, multiple emitters and sensors which may emit/detect different light with a single wavelength each may be provided. This multitude of emitters and sensors may be provided to increase the reliability of the measurement. In more detail, two emitters may be provided which emit light with different wavelengths. Corresponding two sensors may be provided, wherein the first sensor is configured to detect the light which is emitted by the first emitter and the second sensor is configured to detect the light which is emitted by the second emitter. Since a specific element in the aerosol, which is to be detected, may absorb multiple different wavelengths, the detection of this element is increased if the two emitter/sensor-pairs are configured to emit/detect corresponding absorption bands. Alternatively or additionally, multiple emitter/sensor-pairs may be provided to detect multiple components. In more detail, a single emitter/sensor-pair may in this case be configured as a single narrow-band emitter/sensor. Thus, a specific component, i.e. the presence of specific molecules, of the aerosol-generating substrate may be observed with the single narrow-band emitter and sensor. Every single emitter/sensor-pair may be provided to detect a different element of the vaporized aerosol-generating substrate. Also, multiple emitter/sensor-pairs may be provided to reliably detect a specific element of the vaporized aerosol-generating substrate by measuring distinct absorption bands, and further emitter/sensor-pairs may be provided to detect further elements of the vaporized aerosol-generating substrate.

The emitter may be configured as a tunable single narrow-band emitter. This type of emitter is configured adjustable to emit light with different wavelengths. The sensor may be accordingly configured as a tunable single narrow-band sensor, configured to receive light with different wavelengths. By providing a tunable single narrow-band emitter and sensor, different elements within the vaporized aerosol-forming substrate can be determined one after another.

Also, a multiple narrow-band emitter and sensor may be provided. The multiple narrow-band emitter is configured to emit light with different essentially distinct wavelengths. The sensor is accordingly configured to receive light with different essentially distinct wavelengths. Thus, the presence of different elements within the vaporized aerosol-forming substrate can be determined at the same time with high accuracy.

By directly determining the elements of the vaporized aerosol-forming substrate, the operation of the aerosol-generating system may be optimized. For example, if an unwanted product is detected in the vaporized aerosol-forming substrate, the temperature of a heater element may be lowered or the heater element may be deactivated. In this regard, the sensor as well as the emitter may be connected with control circuitry ("electric circuitry"), wherein the control circuitry is further configured to control the flow of electric energy from a power supply to the heater element. Additionally or alternatively, a warning signal may be generated by the control circuitry upon the detection of unwanted products in the vaporized aerosol-forming substrate.

The emitter and the sensor may be arranged isolated from the aerosol. In more detail, the emitter as well as the sensor may be arranged outside of the aerosol chamber or the liquid storage portion, respectively. By arranging the emitter and the sensor isolated from the aerosol, a contamination of the sensor and the emitter may be prevented. Thus, the quality of the measurement is constantly high even if multiple measurements are obtained and even if multiple replaceable aerosol chambers are used.

When the aerosol chamber is provided as part of a liquid storage portion, the liquid storage portion may be provided replaceable. If the liquid aerosol-forming substrate in the liquid storage portion is depleted, the liquid storage portion is detached from the aerosol-generating system and a new liquid storage portion is attached to the aerosol-generating system. The emitter as well as the sensor may be provided as part of the aerosol-generating system, such that no new emitter or sensor must be provided when a new liquid storage portion is provided.

To facilitate that the emitter and the sensor may be provided isolated from the aerosol chamber, the aerosol chamber may have an at least partially transparent housing. By providing an at least partially transparent housing of the aerosol chamber, light, which is emitted by the emitter, may pass into the aerosol chamber and exit the aerosol chamber in the direction of the sensor. The partially transparent housing is arranged between the inner of the aerosol chamber and the emitter and sensor.

The sensor as well as the emitter may be provided as a microelectromechanical system (MEMS) or opto-semiconductor or compound semiconductor or hybrid electronic device. MEMS are very small devices with a typical size between 20 micrometers to a millimeter. Recent developments have led to middle and far infra-red MEMS emitters, coupled with the appropriate detectors. See for example "a MEMS based thermal infra-red emitter for an integrated NDIR spectrometer", published in Microsystem Technologies 18.7-8 (2012): 1147-1154, which is incorporated herein in its entirety. Generally, any suitable emitter and corresponding sensor may be used as long as the sensor and the corresponding emitter are sufficiently small to be employed in the aerosol-generating system. Also, the emitter and the sensor must be able to emit (emitter) and receive (sensor) light with wavelength between 200 nanometer and 30 micrometer in order to examine the aerosol in the aerosol chamber. The emitter or the sensor may have a diameter of 0.5 to 5 millimeter or 1 to 3.5 millimeter or around 2 millimeter. The sensor may comprise at least two sensor-layers, which are each configured to receive light with a certain wavelength. Further, the sensor-layers may be configured to be transparent with respect to light with a certain wavelength. In this way, a single sensor may detect multiple wavelengths and thus examine multiple elements of the vaporized aerosol-forming substrate.

The emitter may be configured to emit light with a wavelength of between 2.8 micrometer and 3.2 micrometer, around 3.0 micrometer and/or of between 6.0 micrometer and 6.6 micrometer, and/or around 6.3 micrometer. By detecting these wavelengths, the presence of water may be determined in the vaporized aerosol-forming substrate. Alternatively or additionally, the emitter may be configured to emit light with a wavelength of between 5.9 micrometer and 6.1 micrometer or around 5.9 micrometer and/or of between 3.3 micrometer and 4.0 micrometer, and/or around 3.7 micrometer. By detecting these wavelengths, the presence of carboxylic acid may be determined in the vaporized aerosol-forming substrate. Carboxylic acid is an undesired product and may be generated, when the heater element gets too hot. The sensor may be configured to receive the respective wavelengths. Similar spectrums, which are well-known by the person skilled in the art, may be detected and determined with respect to different elements in the vaporized aerosol-forming substrate. For example, 1,3-butadiene may be detected. This element is, like carboxylic acid, a representative element which is an undesirable product within the vaporized aerosol-forming substrate. Other elements which can be detected in the above described way are benzene, formaldehyde and nicotine. The respective wavelengths for benzene are around 2.5 micrometer, 3.3 micrometer and 5.7 micrometer. By determining the presence of these components, the quality of the aerosol in the aerosol chamber may be determined. In some example embodiments, multiple wavelengths are measured for each element to increase the reliability of the detection. The sensor may be configured to detect at least one of carbon dioxide ($CO_2$), water, benzene, 1,3-butadiene, formaldehyde, nicotine and carboxylic acid.

Multiple emitters may be provided and arranged in a matrix. The matrix of emitters may be arranged around the aerosol chamber such that essentially half of the surface of the aerosol chamber is covered with the matrix of emitters. The other half of the surface of the aerosol chamber may be covered with a matrix of respective sensors. Thus, 3D-spectroscopy can be conducted in the aerosol chamber in the sense that essentially the whole volume of the aerosol chamber may be subject to the measurement as described above. Consequently, the quality of the measurement, i.e. the accuracy of the measurement, may be improved. In more detail, the whole volume or essentially the whole volume of the aerosol chamber is irradiated with light from the emitters. This light travels through the whole volume of the aerosol chamber and is subsequently received by the matrix of sensors. Thus, the vaporized aerosol-forming substrate in the aerosol chamber may be subject to measurement regardless of the orientation of the aerosol chamber. In some example embodiments, it may be detected if undesired elements are present in specific areas of the aerosol chamber. The sensors may detect that an undesired element is present in the aerosol chamber, if the concentration of this undesired element exceeds a particular (or, alternatively, predefined) threshold in a specific area of the aerosol chamber.

Also, the matrix of emitters and the corresponding sensors may be arranged such that a first row of emitters of the matrix of emitters are configured to emit light with a specific wavelength and a corresponding first row of sensors in the matrix of sensors is configured to receive light with this specific wavelength. In this regard, the first row of emitters may be comprised of narrow-band emitters. A further second row of emitters, which may be likewise narrow-band emitters, may similarly emit light of a different specific wavelength. A corresponding second row of sensors are, similarly, configured to receive this light with a different specific wavelength. In this regard, the rows of sensors may each be comprised of narrow-band sensors. Thus, multiple elements of the aerosol may be measured at the same time by providing multiple emitters and multiple sensors, adapted to emit and receive light with different specific wavelengths. Also, the reliability of the measurement may be enhanced by observing different wavelengths of the spectrum of a single component. Advantageously, however, the used emitters and sensors may be cheap emitters and sensors only adapted to emit (emitters) and receive (sensors) light with specific singular wavelengths.

Multiple emitters and multiple sensors may be arranged around the aerosol chamber, wherein the emitters and the sensors are not arranged in a matrix, but emitter-sensor-pairs are formed able to emit and detect light of a specific wavelength. In this way, multiple elements within the aerosol may be detected or the reliability of the measurement may be enhanced.

According to some example embodiments, a process ("method") for manufacturing an aerosol-generating system is provided, wherein the process comprises the following steps:
  i) providing a housing, enclosing a power supply and electric circuitry for controlling the power supply,
  ii) providing an emitter, configured to emit light,
  iii) providing a sensor, configured to receive light, and
  iv) providing an aerosol chamber, configured to comprise an aerosol, wherein the emitter is further configured to emit light into the aerosol chamber, and wherein the sensor is further configured to receive light from the aerosol chamber and measure at least one wavelength of the spectrum of the received light. The aerosol-generating system may be a handheld aerosol-generating device.

Features described in relation to one aspect may equally be applied to other aspects of some example embodiments.

Figure 1A:
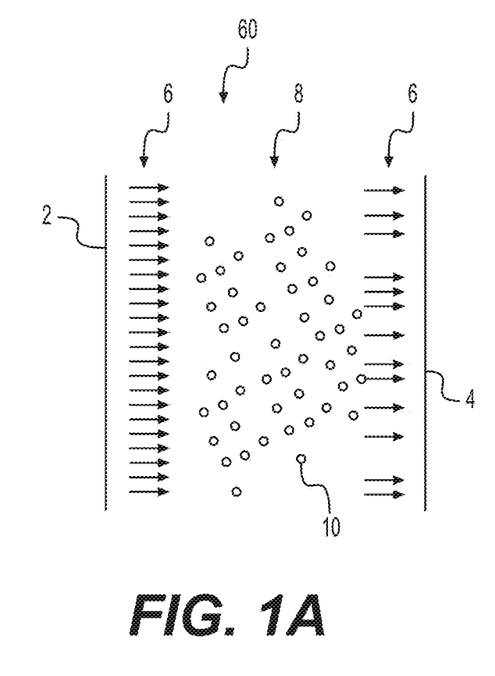
FIGS. 1A and 1B are illustrative views of a handheld aerosol generating-device that includes an schematic emitter and a schematic sensor according to some example embodiments.
Figure 1B:
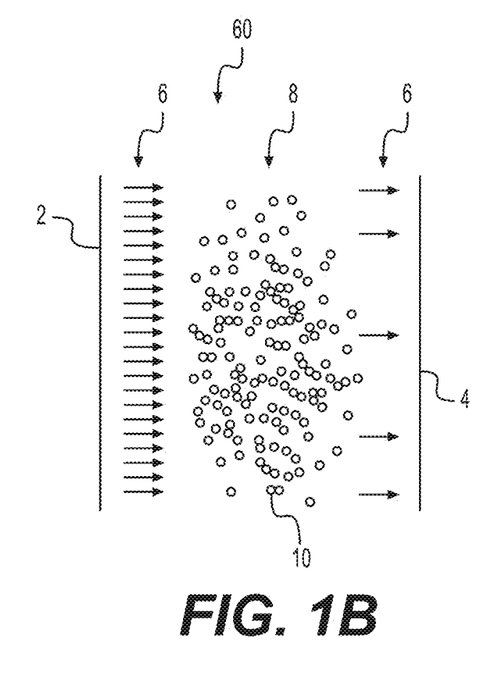

FIGS. 1A and 1B show a handheld aerosol-generating device 60 that includes an emitter 2 and a sensor 4. The emitter emits light 6 in the direction of the sensor 4. The emitted light 6 is directed towards an aerosol chamber 8.

In the aerosol chamber 8, an element 10 of an aerosol-forming substrate is comprised. The element 10 is in FIGS. 1A and 1B depicted as a vaporized element with multiple small particles. FIG. 1A shows the aerosol chamber 8 with a low amount of the element 10 in the aerosol chamber 8. The light, which is emitted by the emitter 2 and directed towards the aerosol chamber 8 is thus only partly absorbed by the element 10.

In more detail, the element 10 is able to at least partly absorb the light which is emitted by the emitter 2. In this regard, the emitter 2 emits light with a specific wavelength or specific wavelengths and the element absorbs this light at least partly. Thus, depending on the amount of the element present in the aerosol chamber 8, more or less light passes through the aerosol chamber 8. In FIG. 1A, a relatively low amount of the element 10 is present in the aerosol chamber 8. Thus, a large amount of the light reaches the sensor 4. The sensor 4 therefore detects that a low amount of the element 10, or no element 10, is present in the aerosol chamber 8. To increase the reliability of the measurement, multiple wavelengths are emitted by the emitter 2 and received by the sensor 4 such that the absorption spectrum of the element 10, and thus the element 10 itself, can be unambiguously detected.

Figure 7:
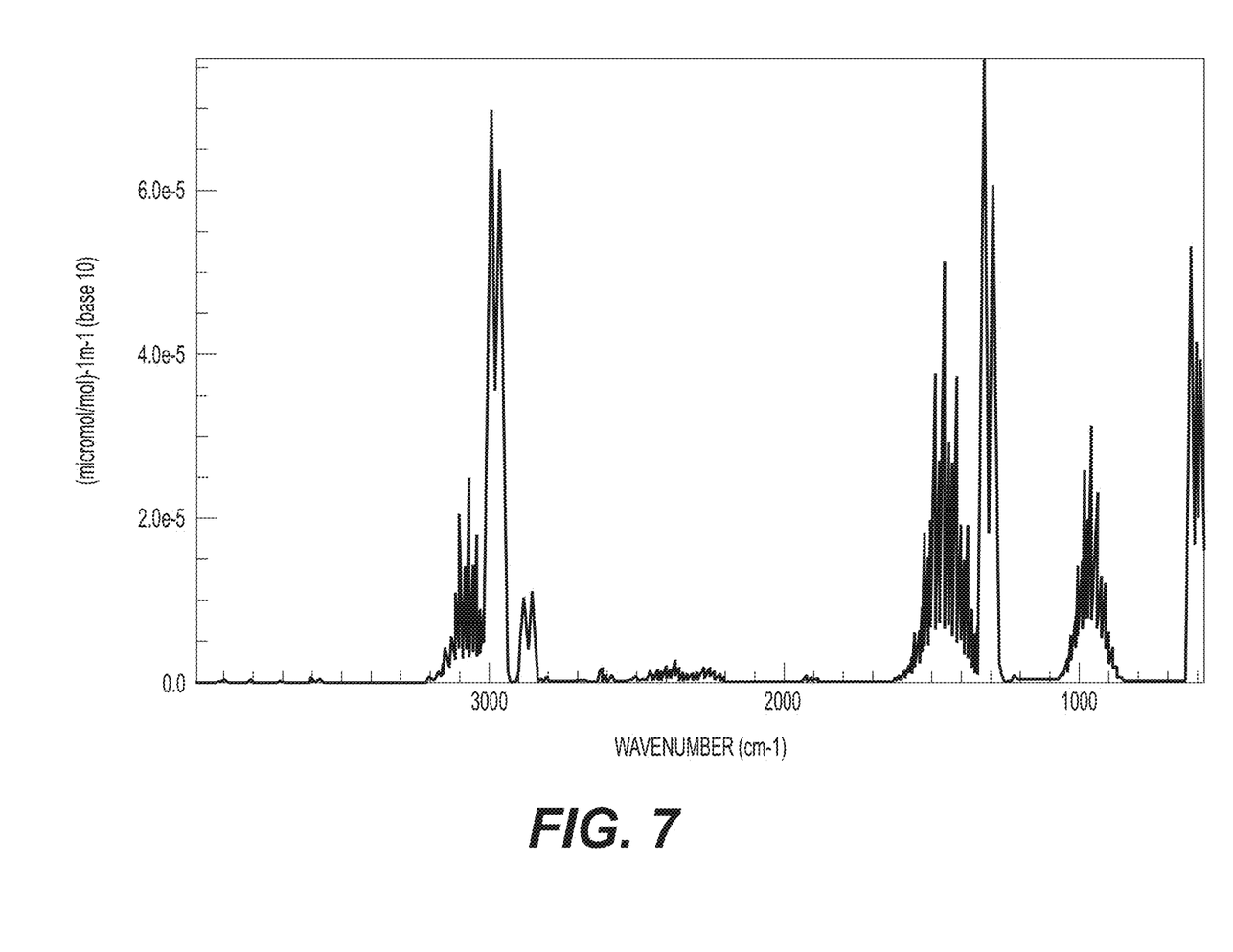
FIG. 7 is an IR spectroscopy from the Wikipedia Article "Infrared spectroscopy"

Thus, an IR-absorption spectrum is measured by the sensor 4. An IR-absorption spectrum according to some example embodiments is depicted in FIG. 7, which shows a sample of an IR spectrum for bromomethane (CH3Br) taken from the Wikipedia Article "Infrared spectroscopy". FIG. 7 clearly shows absorption peaks around 3000, 1300, and 1000 centimeter$^{-1}$ (on the horizontal axis) with different amplitudes. Similar IR-spectrums are created for each element in the aerosol, wherein these spectrums superimpose to form a single spectrum for the aerosol. Multiple peaks and peak-amplitudes are measured by the sensor 4 in this spectrum for the at least one element to be detected to reliably detect the presence and the amount of this component.

In FIG. 1B, a relatively high amount of the element 10 is present in the aerosol chamber 8. Thus, a low amount of the light 6 reaches the sensor 4. The sensor 4 therefore detects that a high amount of the element 10, or that the element 10, is present in the aerosol chamber 8.

The amount of the element 10 present in the aerosol chamber 8 is indicative of the amount of an undesired products in the vaporized aerosol-forming substrate.

Figure 2:
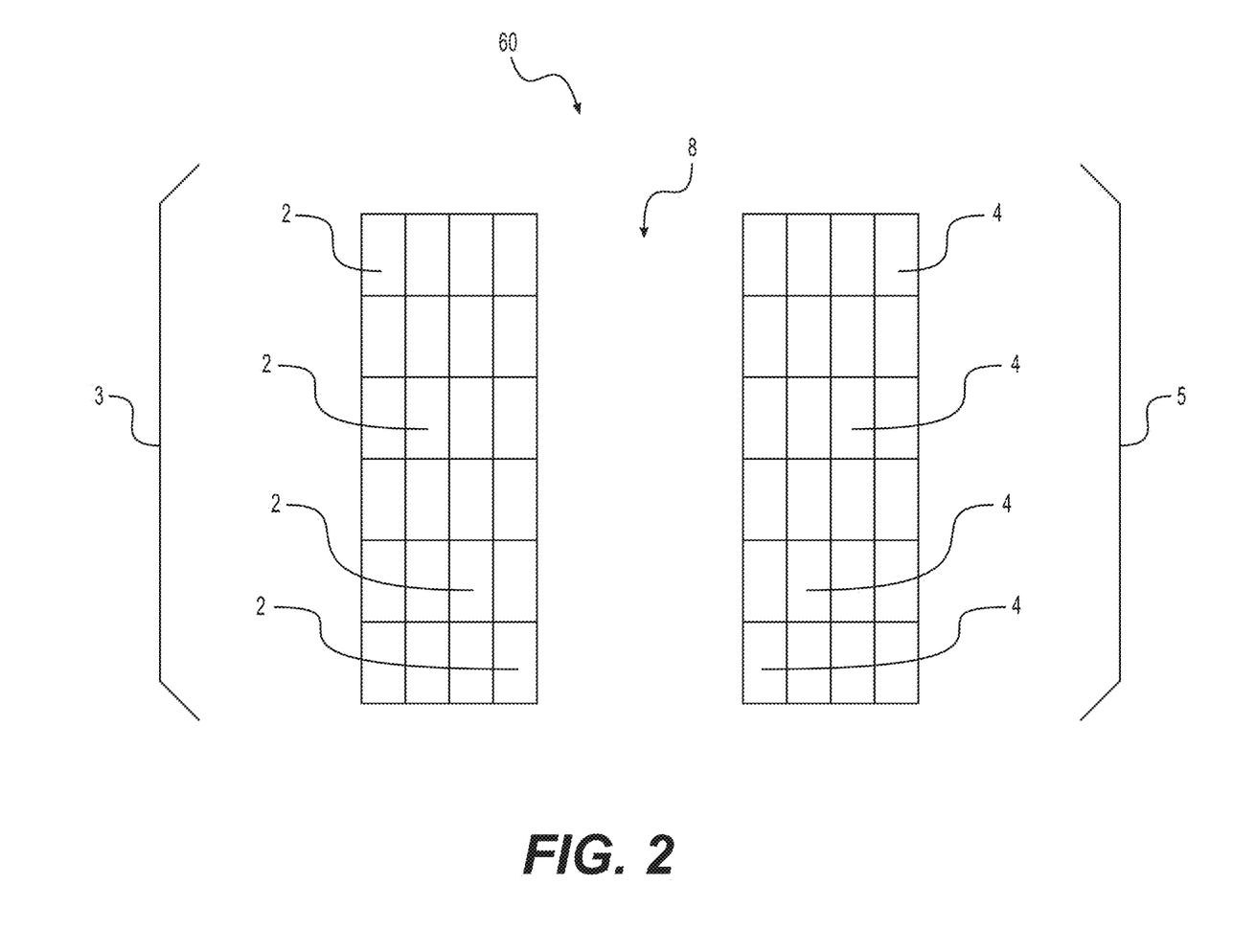
FIG. 2 is an illustrative view of a matrix of emitters and sensors according to some example embodiments.
Figure 4:
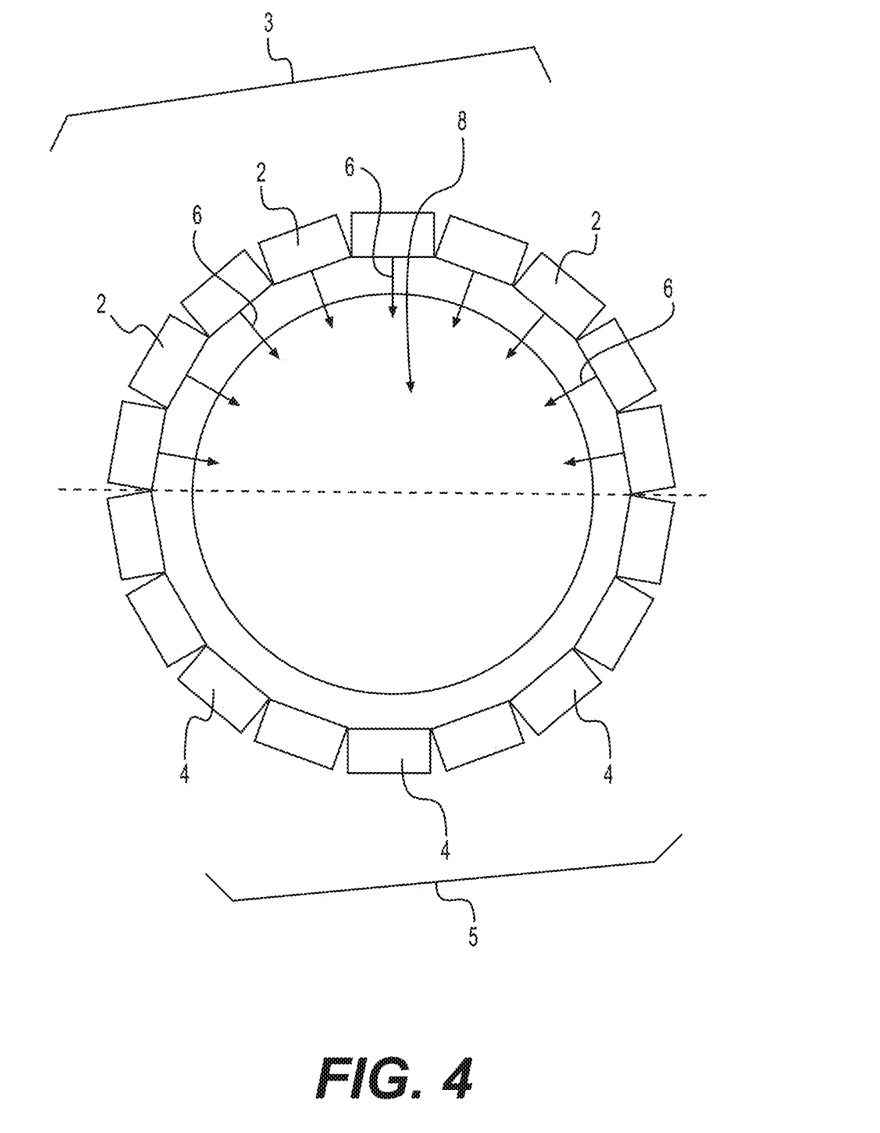
FIG. 4 is an illustrative view of a sensor according to some example embodiments.

FIG. 2 shows some example embodiments of a handheld aerosol-generating device 60 in which multiple emitters 2 and multiple sensors 4 are provided ("located") in respective arrays ("matrices") 3 and 5. As shown in FIG. 2, a handheld aerosol-generating device 60 may include more than two emitters 2 and more than two sensors 4. The emitters 2 as well as the sensors 4 are provided in a matrix. The emitters 2 are arranged around the aerosol chamber 8 as shown in FIG. 4. Thus, the emitters 2 are provided to emit light into the aerosol chamber 8. To enable that, the aerosol chamber 8 is at least partly transparent. By providing multiple emitters 2 and arranging the emitters 2 in a matrix 3 around the aerosol chamber 8, the whole interior of the aerosol chamber 8 can be irradiated with the light of the emitters 2.

Consequently, a matrix 5 of sensors 4 is provided in some example embodiments such as shown in FIG. 2. The sensors 4 are also arranged around the aerosol chamber 8 such as shown in FIG. 4. The sensors 4 are arranged opposite the emitters 2 so that the light emitted by the emitters 2 is radiated into the aerosol chamber 8 and subsequently received by the sensors 4. If a high amount of a certain absorbing element is present in the aerosol chamber 8, only a low amount of or even no light passes through the aerosol chamber 8 to be detected by the sensors 4. Then, the sensors 4 detect that a high amount of the absorbing element is present in the aerosol chamber 8. Thus, the quality and amount of aerosol in the aerosol chamber 8 can be determined with high accuracy. In some example embodiments as shown in FIG. 2, the emitters 2 are configured to emit light with a specific wavelength and the sensors 4 are configured to receive and detect light with the same specific wavelength.

Figure 3:
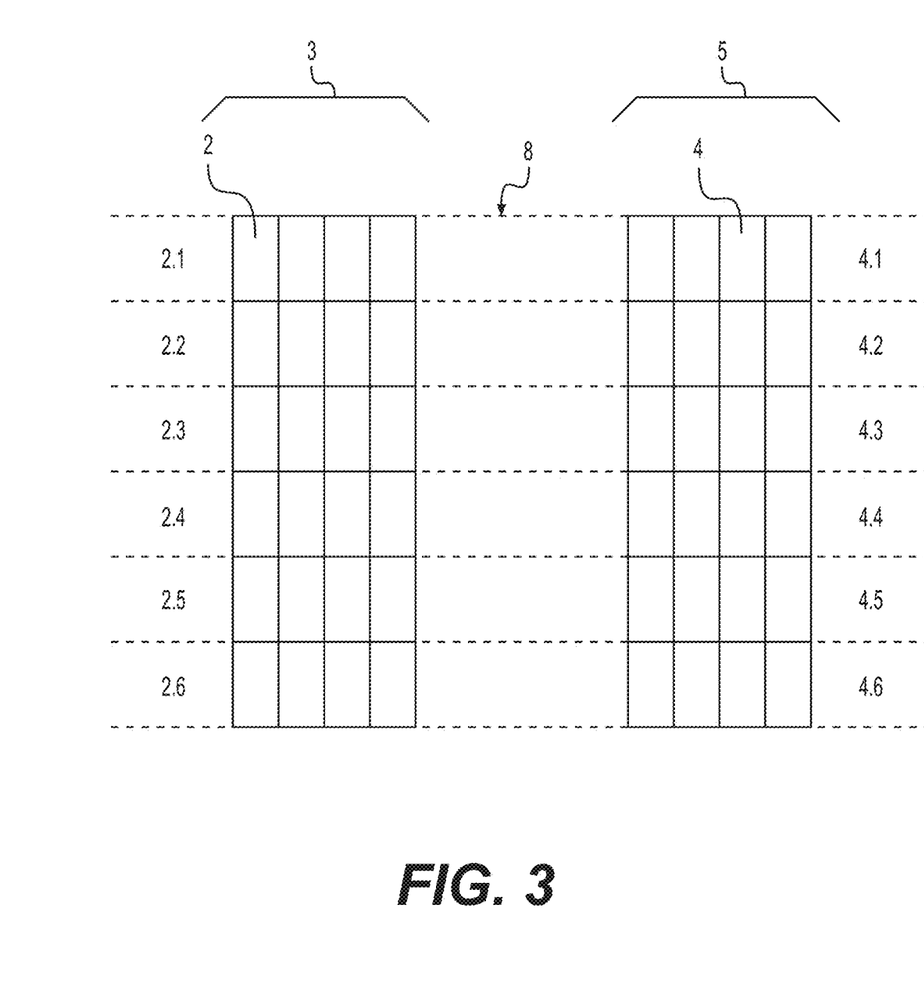
FIG. 3 is an illustrative view of a matrix of emitters and sensors surrounding an aerosol chamber of an aerosol-generating system according to some example embodiments.

FIG. 3 shows some example embodiments in which multiple emitters 2 and multiple sensors 4 are provided in respective matrixes 3 and 5. In contrast to some example embodiments as shown in FIG. 2, the emitters 2 are not configured to emit light of ("having") the same specific wavelength. Rather, the emitters 2 in the matrix 3 as shown in FIG. 3 are arranged in rows 2.1 to 2.6, wherein each row of emitters 2 consists of emitters 2 which are configured to emit light of ("having") the same specific wavelength. A different row of emitters 2 consists of emitters 2 which are configured to emit light of a different specific wavelength. Opposite of the emitters 2 are arranged sensors 4 of matrix 5 which are configured symmetrical in rows 4.1 to 4.6. That is, if a first row 2.1 of emitters 2 of matrix 3 is configured to emit light with a specific first wavelength, the first row 4.1 of sensors 4 of matrix 5 is configured to receive and detect light with this first wavelength. The second row 2.2 of emitters 2 and the second row 4.2 of sensors 4 are configured to emit/receive light with a specific second wavelength. Different absorption bands are determined by the different rows of emitters 2/sensors 4.

FIG. 4 shows the distribution of the emitters 2 and the sensors 4 in respective matrices 3 and 5 around the aerosol chamber 8 according to some example embodiments. The emitters 2 as well as the sensors 4 are arranged in the shape of a semicircle (e.g., a semicircular matrix) along the length of the aerosol chamber 8. The emitters 2 are arranged such that they irradiate light 6 into the inner of the aerosol chamber 8. The aerosol chamber 8 is provided transparent such that the light 6 can enter the inner of the aerosol chamber 8. The emitters 2 are provided as wide bandgap MEMS emitters with a diameter of around 2 millimeter such that multiple emitters can be placed around the aerosol chamber 8. The sensors 4 provided as wide bandgap MEMS sensors arranged around the aerosol chamber 8 opposite of the emitters 2 in the shape of a semicircle. The sensors 4 are configured and arranged such that light 6 from the inner of the aerosol chamber 8 can be received by the sensors 4.

Figure 5:
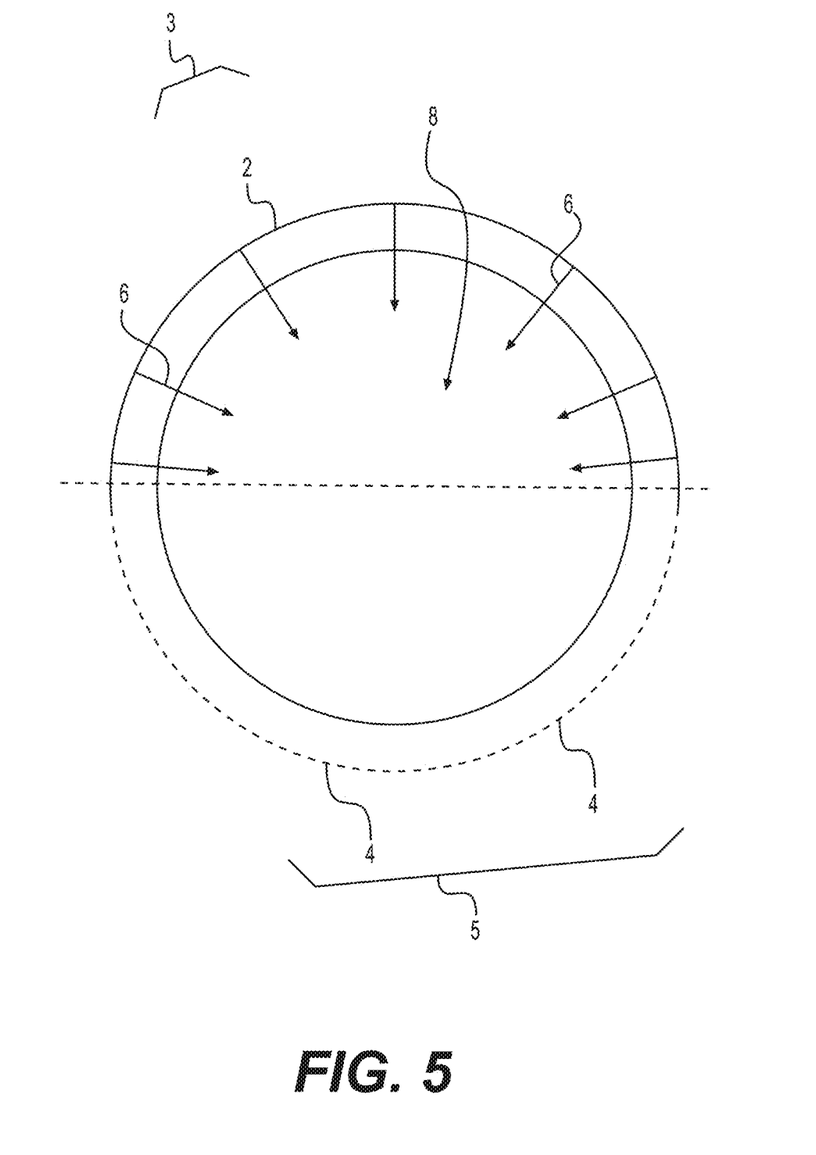
FIG. 5 shows an illustrative view in which the emitters are provided as a layer around the aerosol chamber, according to some example embodiments.

FIG. 5 shows some example embodiments in which the emitters 2 are provided in matrix 3 as a layer around the aerosol chamber 8. In some example embodiments, the layer comprises a matrix 3 of multiple emitters 2, which radiate light 6 into the inner of the aerosol chamber 8 as described above. The sensors 4 or only the sensors 4 can be provided in matrix 5 in a layer instead of distinct separated sensors 4 as depicted in FIG. 4.

Figure 6:
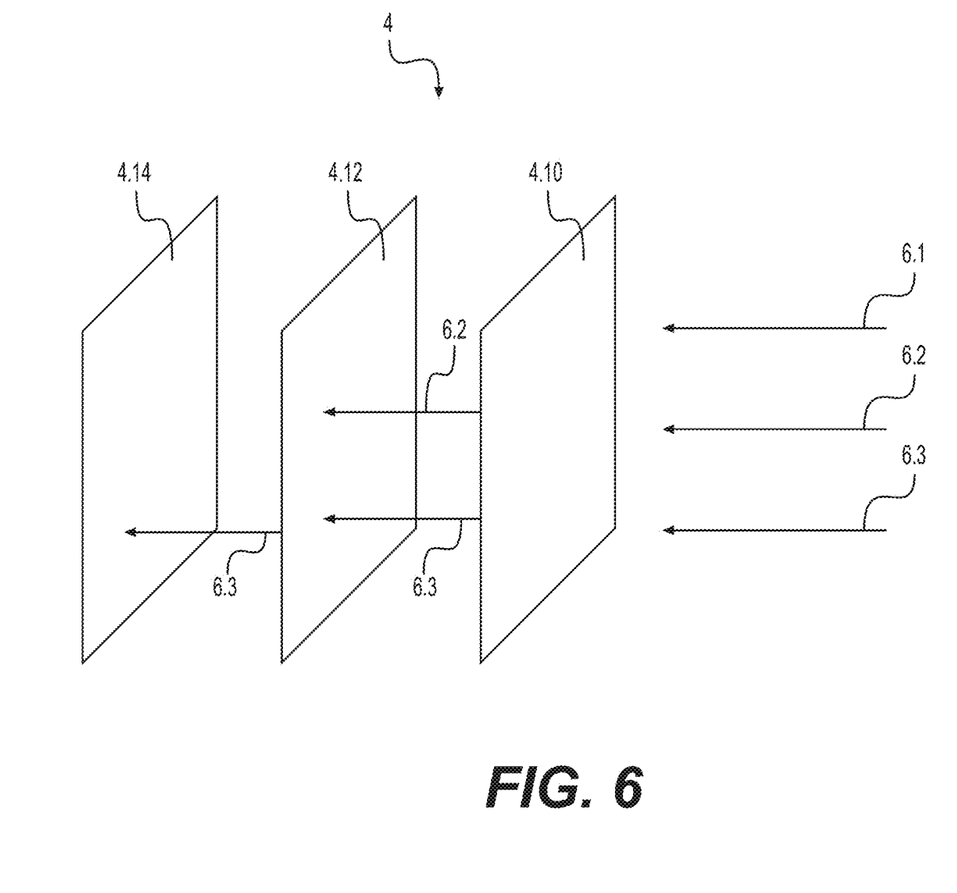
FIG. 6 shows an illustrative view of a sensor, according to some example embodiments, which comprises multiple sensor-layers.

FIG. 6 shows some example embodiments of a sensor 4 which comprises multiple sensor-layers 4.10, 4.12 and 4.14. The different sensor-layers 4.10, 4.12, 4.14 are configured to receive light with a certain wavelength. Further, the sensor-layers 4.10, 4.12, 4.14 are configured to be transparent with respect to light with a certain wavelength. In more detail, a first sensor-layer 4.10 is configured to receive light with a first wavelength 6.1 while being transparent to light with a second wavelength 6.2 and a third wavelength 6.3. Behind the first sensor-layer 4.10, a second sensor-layer 4.12 is arranged. The second sensor-layer 4.12 is configured to receive light with the second wavelength 6.2 while being transparent to light with the third wavelength 6.3. Behind the second sensor-layer 4.12, a third sensor-layer 4.14 is arranged. The third sensor-layer 4.14 is configured to receive light with the third wavelength 6.3. In this way, the single sensor 4 can detect multiple wavelengths and thus examine multiple absorption spectra. In some example embodiments, the sensor 4 comprises at least two sensor-layers.

Figure 8:
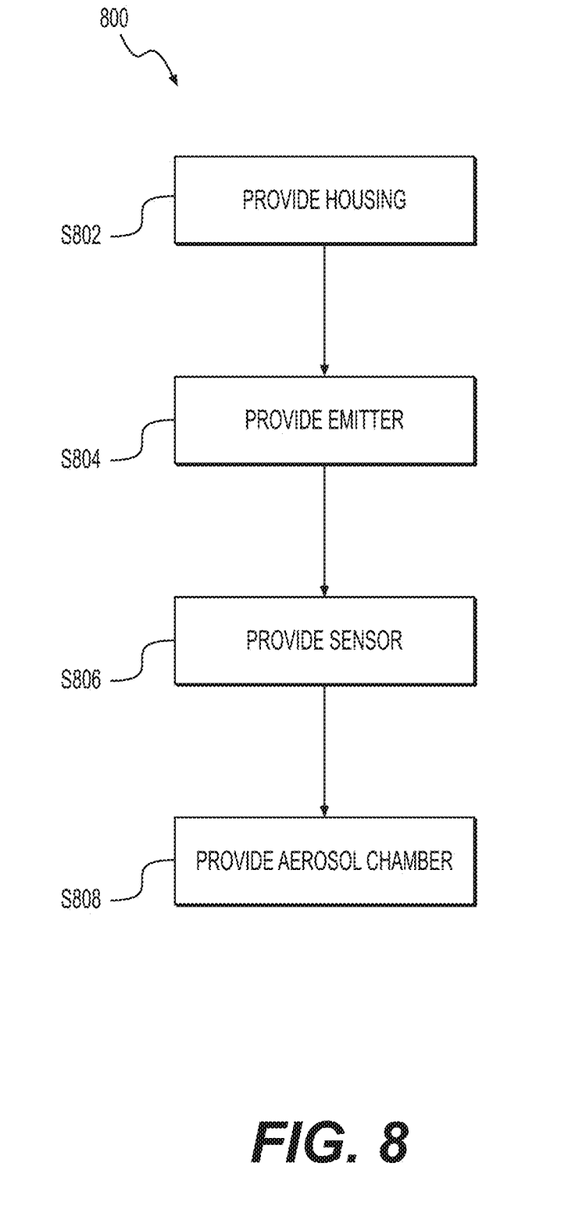
FIG. 8 shows a process a process ("method") for manufacturing an aerosol-generating system according to some example embodiments.

FIG. 8 shows a process a process 800 ("method") for manufacturing an aerosol-generating system according to some example embodiments.

As shown in FIG. 8, the process 800 may include steps ("operations") S802-S808.

At S802, a housing is provided. The housing may enclose a power supply and electric circuitry configured to control the power supply, as described further above.

At S804, an emitter is provided. The emitter may be configured to emit light as described further above. The emitter may be connected to the electric circuitry.

At S806, a sensor is provided. The sensor may be configured to receive light as described further above. The sensor may be connected to the electric circuitry.

At S808, an aerosol chamber is provided. The aerosol chamber may be configured to comprise (e.g., "contain," "hold," etc.) an aerosol as described further above.

The emitter provided at S804 may be configured to emit light into the aerosol chamber provided at S808, and the sensor provided at S806 may be configured to receive light from the aerosol chamber provided at S808 and measure at least one wavelength of the spectrum of the received light. The aerosol-generating system may be a handheld aerosol-generating device as described further above.

Figure 9:
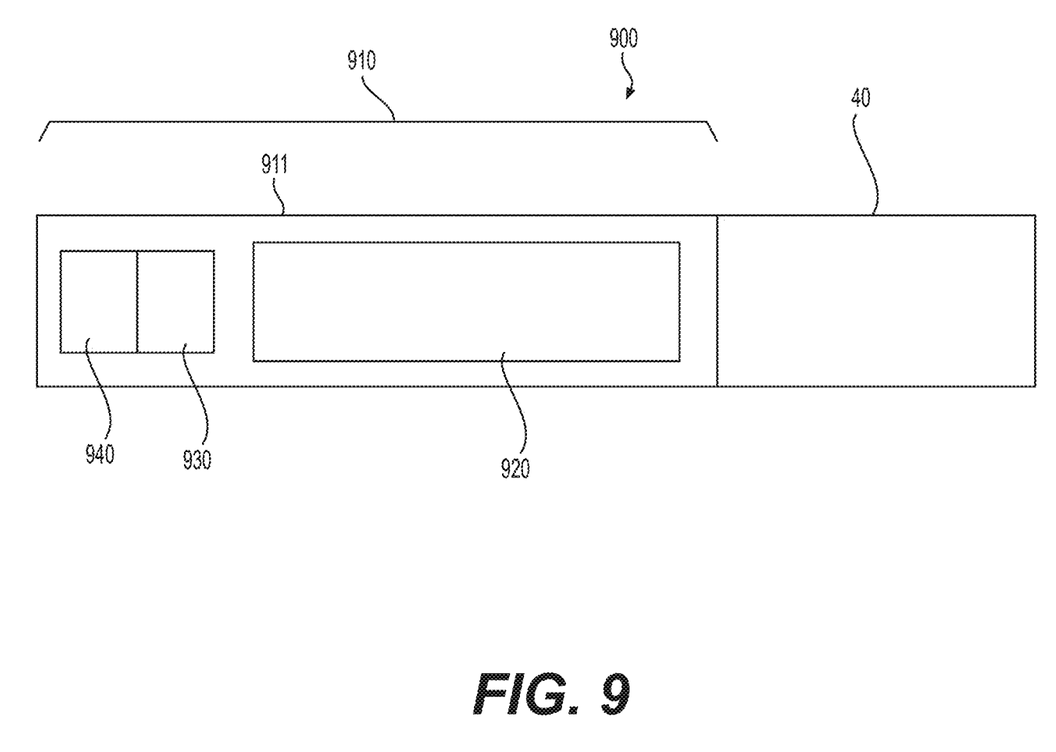
FIG. 9 is a schematic illustration of a handheld aerosol-generating system in accordance with some example embodiments.

FIG. 9 is a schematic illustration of a handheld aerosol-generating system in accordance with some example embodiments.

In at least one example embodiment, as shown in FIG. 9, the aerosol-generating system 900 may include a main unit 910 and a cartridge 40. The main unit 910, also referred to herein as the "device portion," may include a power supply 920, control circuitry 930, and a sensor 940. The aerosol-generating system 900 may be the handheld aerosol-generating-device 60. The control circuitry 930 may be referred to as the aforementioned electric circuitry. The main unit 910 may include a housing 911 that encloses at least the power supply 920 and the electric circuitry (control circuitry 930) and may further enclose the sensor 940. The sensor 940 may be separate from the aforementioned one or more sensors 4 that may be included in an array 5. The cartridge 40 may include an outlet end, a supply of liquid aerosol-forming substrate held in a liquid storage portion, and an electrically operated vaporizer or heater element. At least one of the cartridge 40 and the main unit 910 may include a matrix 3 of one or more emitters 2, a matrix 5 of one or more sensors 4, and the aerosol chamber 8. For example, the aerosol chamber 8, matrix 3 of one or more emitters 2, and matrix 5 of one or more sensors 4 may be included in the cartridge 40.

The example embodiments described above illustrate but are not limiting. In view of the above discussed example embodiments, other embodiments consistent with the above example embodiments will now be apparent to one of ordinary skill in the art.

The invention claimed is:

1. An aerosol-generating device, comprising:
a main device including control circuitry; and
a cartridge engaged with the main device, at least one of the cartridge and the main device including
an aerosol chamber,
an array of at least two emitters arranged outside of the aerosol chamber, and
an array of at least two sensors arranged outside of the aerosol chamber, the array of at least two sensors being arranged opposite the array of at least two emitters,
wherein the cartridge includes an outlet end, a liquid storage configured to hold a supply of liquid aerosol-forming substrate, and a heating element, the heating element being electrically operated.

2. The aerosol-generating device of claim 1, wherein the cartridge includes the aerosol chamber, the array of at least two emitters, and the array of at least two sensors.

3. The aerosol-generating device of claim 2, wherein the main device includes a sensor separate from the array of at least two sensors.

4. The aerosol-generating device of claim 2, wherein the control circuitry is in communication with the array of at least two emitters and the array of at least two sensors.

5. The aerosol-generating device of claim 1, wherein the main device further includes a power supply and a housing, the housing enclosing the power supply and the control circuitry.

6. The aerosol-generating device of claim 1, wherein the array of at least two emitters includes a first emitter and a second emitter, the first emitter configured to emit light having a first wavelength, the second emitter configured to emit light having a second wavelength, the first wavelength being different from the second wavelength.

7. The aerosol-generating device of claim 6, wherein the first wavelength is between 2.8 micrometers and 3.2 micrometers.

8. The aerosol-generating device of claim 7, wherein the second wavelength is between 6.0 micrometers and 6.6 micrometers.

9. The aerosol-generating device of claim 6, wherein the array of at least two sensors includes a first sensor and a second sensor, the first sensor configured to receive the light having the first wavelength, the second sensor configured to receive the light having the second wavelength.

10. A cartridge configured to be engaged with an aerosol-generating device, the cartridge comprising:
an aerosol chamber;
an array of at least two emitters arranged outside of the aerosol chamber;
an array of at least two sensors arranged outside of the aerosol chamber, the array of at least two sensors being arranged opposite the array of at least two emitters;
an outlet end;
a liquid storage configured to hold a supply of liquid aerosol-forming substrate; and
a heating element, the heating element being electrically operated.

11. The cartridge of claim 10, wherein the aerosol chamber is disposed downstream of the liquid storage and upstream of the outlet end.

12. The cartridge of claim 10, wherein the array of at least two emitters includes a first emitter and a second emitter, the first emitter configured to emit light having a first wavelength, the second emitter configured to emit light having a second wavelength, the first wavelength being different from the second wavelength.

13. The cartridge of claim 10, wherein each emitter of the array of at least two emitters is opposite to a corresponding sensor of the array of at least two sensors.

14. An aerosol-generating device, comprising:
a main device including a controller, the controller being configured to actuate an array of at least two emitters arranged outside of an aerosol chamber, and to process signals from an array of at least two sensors arranged outside of the aerosol chamber, the array of at least two sensors being arranged opposite the array of at least two emitters; and
a cartridge engaged with the main device, the aerosol chamber being arranged in one of the main device and the cartridge, the cartridge including an outlet end, a liquid storage configured to hold a supply of liquid aerosol-forming substrate, and a heating element, the heating element being electrically operated.

15. The aerosol-generating device of claim 14, wherein the controller is configured to actuate a first emitter of the array of at least two emitters to emit light having a first wavelength, and to actuate a second emitter of the array of at least two emitters to emit light having a second wavelength, the first wavelength being different from the second wavelength.

16. The aerosol-generating device of claim 15, wherein the controller is configured to processes a first signal from a first sensor of the array of at least two sensors and to process a second signal from a second sensor of the array of at least two sensors, and the controller is configured to determine a presence of an element in the aerosol chamber based on the first signal, the second signal, or the first signal and the second signal.

17. The aerosol-generating device of claim 16, wherein the controller is configured to generate a warning signal based on the presence of the element in the aerosol chamber.

18. The aerosol-generating device of claim 14, wherein the controller is configured to control a flow of electric energy from a power supply housed in the main device to a heater element housed in the cartridge.

* * * * *